(12) United States Patent
Huet et al.

(10) Patent No.: US 6,261,263 B1
(45) Date of Patent: Jul. 17, 2001

(54) HUB OF ARTERIAL PUNCTURE NEEDLE

(75) Inventors: Jean-Max Huet, Clichy; Daniel Rossi, Meriel; Thierry Brinon, Montsoult, all of (FR)

(73) Assignee: Vygon (FR)

( * ) Notice: Subject to any disclaimer, the term of this patent is extended or adjusted under 35 U.S.C. 154(b) by 0 days.

(21) Appl. No.: 09/385,195

(22) Filed: Aug. 30, 1999

(30) Foreign Application Priority Data

Sep. 1, 1998 (FR) .................................................. 98 10904

(51) Int. Cl.$^7$ .................................................. A61M 5/178
(52) U.S. Cl. .................................................. 604/168; 604/264
(58) Field of Search .............................. 604/168.01, 122, 604/126, 411, 264, 164.01, 164.02, 164.03, 164.04, 164.05, 164.06–164.13, 165.01–165.04, 166.01, 167.01–167.06, 272, 171, 118; 606/167, 170, 184, 185

(56) References Cited

U.S. PATENT DOCUMENTS

| | | | |
|---|---|---|---|
| 3,859,998 | * | 1/1975 | Thomas et al. ....................... 604/122 |
| 4,193,399 | * | 3/1980 | Robinson .............................. 604/122 |
| 4,269,186 | * | 5/1981 | Loveless et al. ..................... 604/122 |
| 4,682,980 | * | 7/1987 | Suzuki ................................. 604/122 |
| 5,439,449 | * | 8/1995 | Mapes et al. ......................... 604/164 |

* cited by examiner

*Primary Examiner*—Manuel Mendez
(74) *Attorney, Agent, or Firm*—Mason, Kolehmainen, Rathburn & Wyss

(57) ABSTRACT

A hub (1) of an arterial puncture needle includes a tubular and transparent viewing chamber (5) accessible to the reflux of blood, and a reserve chamber (6) which is leaktight to the ambient air and in air communication with an outlet end (5b) of the viewing chamber. The two chambers form a rigid unit with the hub and have predetermined volumes such that the blood does not reach the air reserve chamber when the systolic pressure is maximal.

8 Claims, 1 Drawing Sheet

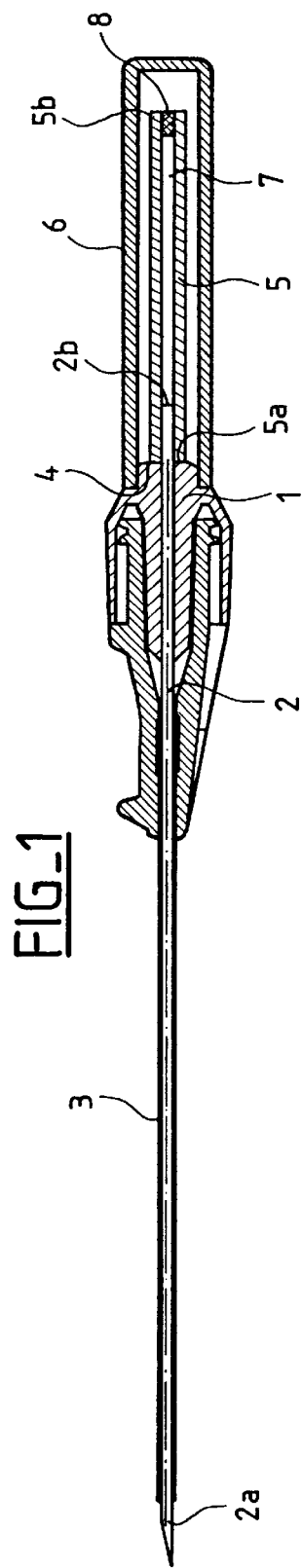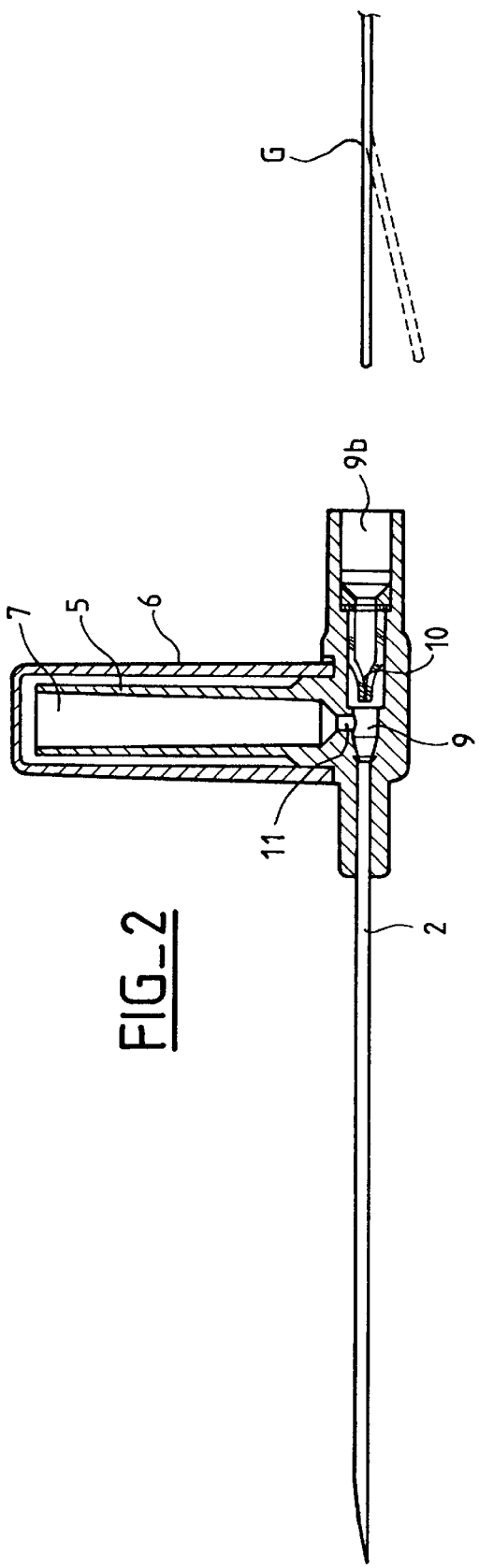

HUB OF ARTERIAL PUNCTURE NEEDLE

FIELD OF THE INVENTION

The invention concerns the hub of an arterial puncture needle.

BACKGROUND OF THE INVENTION

Arterial puncture needles are used in particular to permit introduction of a catheter into an artery. The catheter is advanced into the artery by sliding on the needle which guides it (called the short catheter method) or by sliding on a metal guide introduced beforehand into the artery via the puncture needle (called the Seldinger method).

The practitioner using the arterial puncture needle knows that the needle is in fact in place in the artery by observing the blood exiting from the needle. In particular, the blood will have pulsatile flow if the needle is in an artery.

For visualizing the pulsatile flow of blood without risk of the practitioner coming in contact with the blood, it is known, in the case of a short catheter, to provide the needle hub with a tubular and transparent viewing chamber. This chamber is accessible, via an inlet end, to the reflux of blood in the needle and closed at an opposite outlet end by a plug which is leaktight to the blood but permeable to the air.

The arterial pressure, which is greater than the atmospheric pressure, causes the reflux of blood to completely fill the viewing chamber once the needle penetrates into the artery.

If the puncture is to be repeated, the practitioner can remove the plug in order to empty the chamber and thereafter can put the plug back in place. In such a case, the practitioner is unable to monitor the new introduction of the needle into the artery because the walls of the viewing chamber are already red with the blood from the previous puncture. On the other hand, the practitioner can leave the proximal end of the needle open allowing the blood to escape freely from the hub.

SUMMARY OF THE INVENTION

The object of the present invention is to make it possible to visualize the flow of blood even in this case and, more generally, throughout the duration of the operation of introducing the catheter into the artery, without manipulation and without contact with the patient's blood.

It has been proposed to provide the hub with means for creating a counter-pressure sufficient to maintain an air pressure at the outlet end of the viewing chamber with the amount of this air pressure varying under the effect of the variations in the pressure of the blood in the needle. These means comprises an air reserve chamber which is leaktight to the ambient air, situated outside the viewing chamber and in air communication with the outlet end of the viewing chamber (see, for example, U.S. Pat. No. 5,439,449). In this known solution, the air reserve chamber is formed by an elastomeric reservoir connected to the hub by a flexible connection and protected by a casing.

The present invention aims to provide a simple solution such that the device as a whole is easy to handle, without a flexible attachment which can be awkward when performing the puncture, and functions reliably.

According to the invention, this is achieved by using a viewing chamber which forms a rigid unit with the hub and with the air reserve chamber. The volumes of the chambers are predetermined such that the blood is visible in the viewing chamber when the diastolic pressure is minimal and such that the blood does not reach the air reserve chamber when the systolic pressure is maximal.

When the needle penetrates into the artery, the blood flows back into the needle and only partially fills the viewing chamber. The air contained initially is compressed inside the air reserve chamber and the variation in arterial pressure causes the blood to move inside the viewing chamber.

To make the device more compact, it is advantageous, according to one particular feature of the invention, to place the air reserve around the viewing chamber.

BRIEF DESCRIPTION OF THE DRAWINGS

Two embodiments of a needle hub according to the present invention will be described hereinafter with reference to the figures of the attached drawing, in which FIG. 1 is a longitudinal section through a short catheter hub, and FIG. 2 is a diagram of a puncture needle hub used for fitting a catheter by the Seldinger method.

DETAILED DESCRIPTION

The catheter needle hub represented in FIG. 1 is a tubular hollow body or hub (1) of synthetic material through which a needle (2) passes. The distal end (2a) of the needle (2) is bevelled.

A catheter tube (3) is affixed to the needle. Extending from a proximal end (4), of the hub (1) is a tubular and transparent viewing tube (5) which has a distal inlet end (5a) into which the proximal end (2b) of the needle fits. The viewing tube (5) is surrounded by an outer air reserve tube (6) which is airtight and which is clipped and/or bonded onto the hub. These two tubes communicate with one another via the proximal end (5b) of the viewing tube (5) which is not airtight. These two tubes, are rigid, form a rigid unit with the hub, are made of a transparent material and have a length of several centimetres. If so desired, the outlet end (5b) of the inner tube (5) is closed by a plug (8) which stops (is impermeable to) the blood but which allows the air to pass therethrough.

Under the effect of the blood pressure, the blood flows back into the inner viewing tube (5) without reaching its proximal end (5b) on account of the pressure of the compressed air in the outer tube (6).

The space (7) in the inner tube (5) between the column of blood and the proximal end (5b) of the tube makes it possible to follow the movement of the blood under the effect of the variations in the blood pressure.

In the embodiment in FIG. 2, the hub (1') includes a main channel (9), at one end of which the needle (2') is mounted, and the opposite end (9b) of which is open to permit engagement therein of a sleeve (G) for guiding the catheter. A nonreturn valve (10) is placed in this channel while the channel (9) between the mounting end of the needle (2') and the valve (10) communicates via a lateral passage (11) with a transverse viewing tube (5') about a space 7' and is surrounded by an outer air reserve tube (6'). The tubes (5) and (6') have the roles of the tubes (5) and (6), respectively, of the preceding embodiment.

As in the previous embodiment, a plug leaktight to blood but not airtight can be placed at the end of the inner tube (5') which opens into the outer tube (6').

The invention is not limited to these illustrative embodiments.

We claim:

1. A hub of an arterial puncture needle comprising a tubular and transparent viewing chamber accessible via an inlet end to reflux of blood in the needle under the effect of arterial pressure, pressure means being provided to create at an outlet end of the viewing chamber a counter-pressure sufficient to maintain a pressure at the outlet end, the pressure varying under the effect of the variations in the pressure of the blood in the needle, said pressure means comprising an air reserve chamber which is leaktight to ambient air, which is situated outside the viewing chamber and which is in air communication with the outlet end of the viewing chamber, the air reserve and viewing chambers being rigid and forming with the hub a rigid unit wherein the air reserve chamber is disposed concentrically about the viewing chamber and the volumes of the chambers are predetermined such that the blood does not reach the air reserve chamber when the systolic pressure is maximal.

2. A hub according to claim 1 wherein the outlet end of the viewing chamber is closed by a plug which is leaktight to the blood but permeable to the air.

3. A hub according to claim 1 wherein the viewing chamber extends along the axis of the needle.

4. A hub according to claim 1 wherein the viewing chamber extends along the axis of the needle.

5. A hub according to claim 1 wherein the viewing chamber extends transverse to the axis of the needle.

6. A hub according to claim 1 wherein the viewing chamber extends transverse to the axis of the needle.

7. A hub according to claim 5 including a channel which communicates at one end with the needle and which has an opposite open end and further including a nonreturn valve disposed in said channel and wherein the viewing chamber opens into the channel between the nonreturn valve and the end of the channel which communicates with the needle.

8. A hub according to claim 6 including a channel which communicates at one end with the needle and which has an opposite open end and further including a nonreturn valve disposed in said channel and wherein the viewing chamber opens into the channel between the nonreturn valve and the end of the channel which communicates with the needle.

* * * * *